(12) United States Patent
Barber et al.

(10) Patent No.: US 7,157,920 B2
(45) Date of Patent: Jan. 2, 2007

(54) NON-DESTRUCTIVE MONITORING OF MATERIAL INTEGRITY

(75) Inventors: Brent W. Barber, Tolland, CT (US); Jerrol W. Littles, South Glastonbury, CT (US)

(73) Assignee: United Technologies Corporation, Hartford, CT (US)

( * ) Notice: Subject to any disclaimer, the term of this patent is extended or adjusted under 35 U.S.C. 154(b) by 0 days.

(21) Appl. No.: 10/915,515

(22) Filed: Aug. 10, 2004

(65) Prior Publication Data

US 2006/0033504 A1 Feb. 16, 2006

(51) Int. Cl.
G01R 31/26 (2006.01)

(52) U.S. Cl. .......................... 324/700; 324/718

(58) Field of Classification Search ................ 324/700, 324/718; 73/799
See application file for complete search history.

(56) References Cited

U.S. PATENT DOCUMENTS

| | | | |
|---|---|---|---|
| 2,326,352 A | 8/1943 | Greanslade | |
| 2,368,119 A | 1/1945 | De Lanty et al. | |
| 2,735,754 A * | 2/1956 | Dravnieks | 324/700 |
| 2,964,796 A * | 12/1960 | Press | 264/313 |
| 3,636,441 A * | 1/1972 | Fujimura et al. | 324/718 |
| 3,721,897 A * | 3/1973 | Edling | 324/715 |
| 4,656,595 A | 4/1987 | Hognestad | |
| 4,677,855 A | 7/1987 | Coffin, Jr. et al. | |
| 4,764,970 A | 8/1988 | Hayashi et al. | |
| 4,800,165 A * | 1/1989 | Oka et al. | 205/777 |
| 5,243,298 A * | 9/1993 | Runner | 324/700 |
| 5,317,925 A * | 6/1994 | Hayashi et al. | 73/799 |
| 5,728,943 A * | 3/1998 | Colter et al. | 73/799 |
| 6,320,391 B1 * | 11/2001 | Bui | 324/537 |
| 6,476,624 B1 | 11/2002 | Chuman et al. | |
| 6,628,111 B1 * | 9/2003 | Shapiro et al. | 324/71.2 |
| 2003/0169058 A1* | 9/2003 | Pierre et al. | 324/700 |
| 2004/0061510 A1* | 4/2004 | Hands | 324/700 |
| 2004/0207413 A1* | 10/2004 | Burns et al. | 324/700 |

FOREIGN PATENT DOCUMENTS

| | | |
|---|---|---|
| DE | 3434801 | 4/1986 |
| JP | 58196450 | 11/1983 |
| WO | WO 9119968 A1 * | 12/1991 |

* cited by examiner

*Primary Examiner*—Anjan Deb
(74) *Attorney, Agent, or Firm*—Wall Marjama & Bilinski LLP

(57) ABSTRACT

A component which is known to have particular degradation characteristics is instrumented to provide an electrical potential across a section in which a degradation is likely to occur. The potential drop across the component is then monitored to determine when, and the degree to which, the degradation occurs. Predetermined limits are established such that when the degradation level reaches a limit, the component is repaired or replaced.

28 Claims, 3 Drawing Sheets

NON-DESTRUCTIVE MONITORING OF MATERIAL INTEGRITY

BACKGROUND OF THE INVENTION

This invention relates generally to non-destructive testing of component materials subject to degradation and, more particularly, to a non-destructive monitoring of aircraft engine components for possible degradation.

In the upkeep and maintenance of most mechanical and/or electrical apparatus, repair and/or replacement of parts does not occur until a failure causes the apparatus to be inoperable. At that time, inspection is made to determine the particular failure that has occurred, and a replacement part is installed to bring the apparatus to an operable condition.

In contrast, there are certain types of apparatus which, because of safety concerns, are preferably not permitted to have their components reach the level of failure. An aircraft gas turbine engine is such an apparatus. Here, it has become common practice to predict, on the basis of component life histories the operating life of a component and, to periodically repair or replace such a component prior to the time in which it is predicted to fail. In this manner, a useful life of the component is approximated while minimizing the risk of failure.

In a turbine engine, component cracking (e.g. creep, low cycle fatigue (LCF), high cycle fatigue (HCF), stress corrosion cracking is usually associated with high stress risers (i.e. radius, bolt holes, flanges, etc) high temperatures, processing defects or combinations thereof. These stress locations can be identified by analysis or by experience from field failures. To mitigate risk from cracking, service life limits are determined for many components such as disks, blades, shafts, air seals, and tubing, and are removed from service before long cracks have a chance to evolve.

In the field of fracture mechanics, electrical potential difference is an established laboratory technique for determining crack growth rate characteristics in electrically conducting materials. The electrical field in these specimens is disturbed by the initiation of a crack and varies predictably with increasing crack size. In a case where constant current is imposed through the specimen, the potential drop across the crack plane will increase with increasing crack size. This predictable response to the electrical field is used to relate a change in voltage to crack size and is used as an automating means of continuously monitoring crack size.

SUMMARY OF THE INVENTION

Briefly, in accordance with one aspect of the invention, a component which is known to have a particular degradation characteristics is instrumented such that an electrical potential is established across a section in which a degradation is likely to occur with time of operation. The potential drop across the component is then monitored to determine when, and the degree to which, the degradation occurs.

By yet another aspect of the invention, when the degradation of the component reaches a predetermined level, with the level being predetermined by a review of historical occurrences, the component is repaired or replaced.

In accordance with yet another aspect of the invention, a flexible fuel line assembly having a polytetrafluoroethylene (PTFE) tube core reinforced on its outer diameter with a stainless steel wire braid is instrumented for monitoring the potential drop thereacross to determine the occurrence of progressive wire strand breakdown which, if allowed to continue would result in failure of the PTFE tube core. When the number of wire strand failures reaches a predetermined level, the fuel line assembly is replaced.

In the drawings as hereinafter described, a preferred embodiment is depicted; however, various other modifications and alternative constructions can be made thereto without departing from the true spirit and scope of the invention.

DESCRIPTION OF THE PREFERRED EMBODIMENT

The present method can be effectively used with any component that undergoes a cross sectional area change due to the progression of a crack, pitting, corrosion, erosion, wear, etc. The principal involved is that a change in the effective cross sectional area in an electrically conductive component results in a change in its electrical resistance, such that a monitoring of the electrical resistance can be used to effectively monitor the component's health state.

Figure 1:
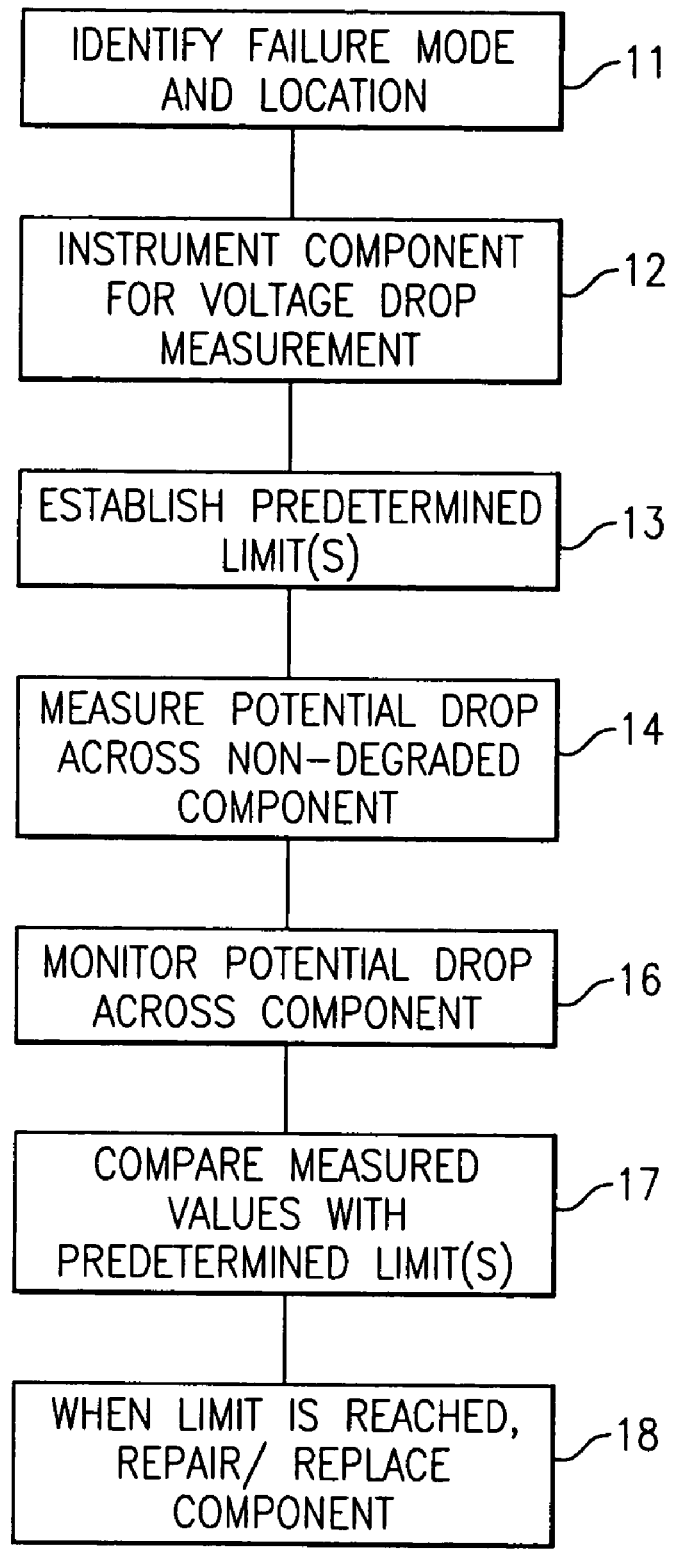
FIG. 1 is a representative flow chart illustrating a process in accordance with an embodiment of the present invention.

The steps of the process will now be described with reference to FIG. 1. Having identified a component that is prone to have a gradual degradation resulting from normal use, it is first necessary to identify the particular failure mode that is likely to occur as set forth in block 11. This includes not only the particular location on the component but also the particular direction of propagation of the fault.

The next step, as shown in block 12, is to instrument the component to enable the measurement of its electrical resistance or potential drop thereacross. Preferably, the potential drop is measured between two points having a connecting line that is aligned substantially normally to the direction of the fault propagation. That is, to monitor the condition of a crack, the direction of the crack should be substantially normal to the direction of the line connecting the two measurement points such that as the crack increases in width, the potential drop between the two measurement points will be proportionally increased.

It is necessary to determine, for the particular fault that is likely to occur to the component, a representative potential drop limit that would indicate the degree to which a degradation, such as how big a crack is allowed to grow, is allowed to occur without any substantial risk of failure. This is accomplished in step 13. This limit may relate to the size of the crack or the speed of propagation, for example.

In order to have a base in which the operational measurements will relate, it is necessary to first measure the potential drop across the component when in the non-degraded condition as shown in step 14. Any increase in the potential drop that is subsequently measured will be an indication of the degradation that occurs during operational use.

The instrumentation is then maintained in its installed position such that the potential drop across the component can be continued to be monitored on a real time basis during operational use of the component as shown in block 16. Thus, at any time, the specific reading can be considered and compared with historical data to determine whether the condition of component is on track with the predicted performance or whether it may be degrading at a rate that is indicative of a degradation rate that is accelerated from the predicted rate and therefore calls for taking corrective action. The step at block 17 is therefore provided to compare the measured values with the value(s) determined in block 13, and these values may be indicative of an accumulative limit on the crack size or, alternatively, indicative of an unacceptable propagation rate. In either case, when such limit is reached, indicating that action should be taken, the component should be repaired or replaced as set forth in block 18.

It should be recognized that the above method may be used to monitor any component that has a failure mechanism that evolves from loss of material or change in cross sectional area. For purposes of explanation, the process will now be described in terms of use with a particular application relating to an engine having a fuel line that is subject to degradation.

Figure 2:
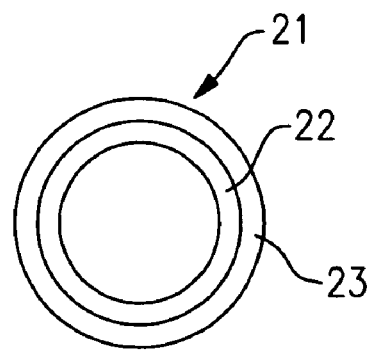
FIG. 2 is a sectional view of a fuel line assembly to be monitored in accordance with an embodiment of the present invention.
Figure 3:
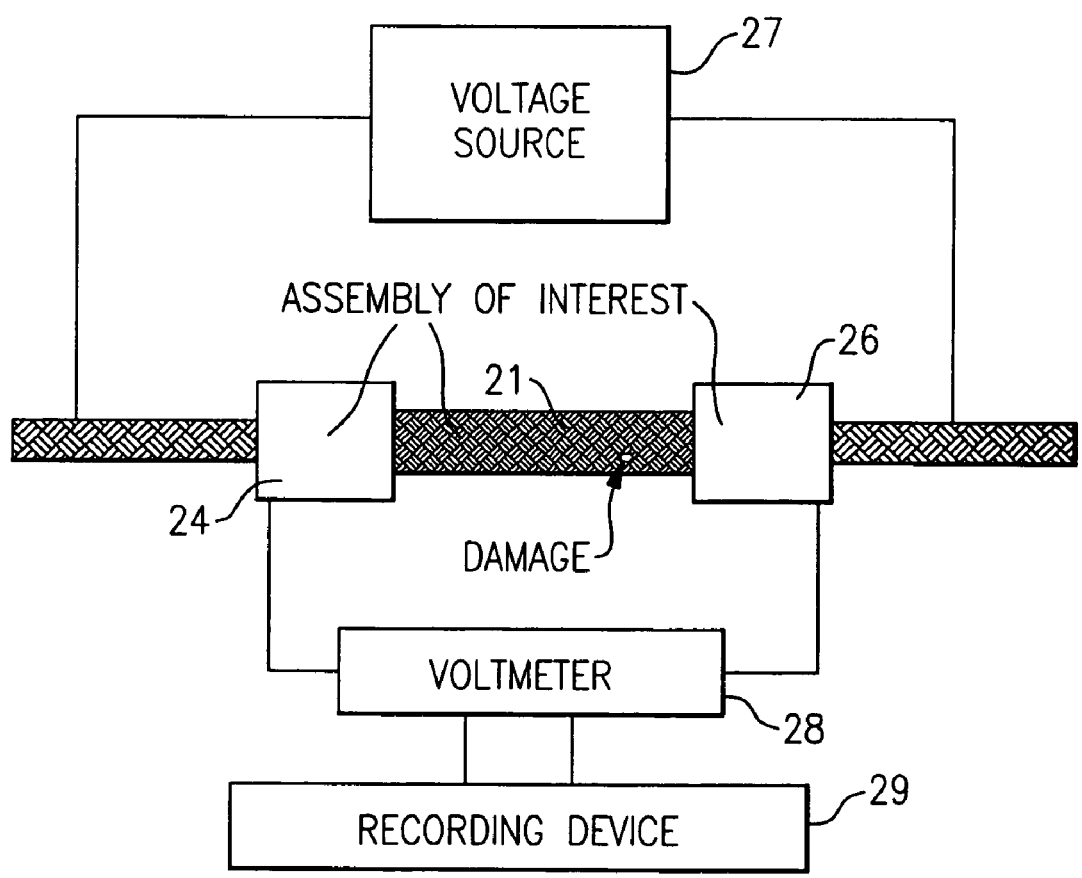
FIG. 3 is a schematic illustration of a component as instrumented in accordance with one embodiment of the present invention.

Referring now to FIGS. 2 and 3, a flexible fuel line assembly is shown at 21 which consist of a PTFE tube core 22 reinforced on its outer diameter with a stainless steel wire braid 23. Typical of such an assembly, the structure of the wire braid 23 consists of approximately 175 strands of 0.005 inch conductive, stainless steel wire. The stainless steel wire 23 and the PTFE 22 are held together at each end with a crimped sleeve tube connector indicated at 24 and 26, respectively. An example of such a flexible hosing is part no. 1A9357 available from Titeflex Corporation, Springfield, Mass.

An identified potential failure mode of the flexline fuel line assembly 21 is a corrosion of the stainless steel braid followed by a progressive breakage of the individual stainless steel wires. The progressive failure of the braid 23 could eventually result in the rupture of the inner PTFE core 22, resulting in fluid leakage. The present method monitors and detects the progression of damage to the wire braid 23 and allows for the replacement of the fuel line assembly 21 in a timely manner before the integrity of the PTFE core 22 can be comprised.

In FIG. 3, there is shown a schematic illustration of the non-destructive instrumentation arrangement for monitoring the condition of the fuel line assembly 21 in accordance with the method as described hereinabove. Here, a DC current source 27 is connected to provide a voltage drop across a 4 inch strand of the fuel line assembly 21, with a constant current of 1 amp flowing through the stainless steel wire braid 23. The voltage drop across the assembly is then continually measured by the volt meter 28 and recorded by a recording device 29. Such an assembly and instrumentation can then be used during the period in which the fuel line assembly 21 is assembled and operating with an engine in typical use. This allows monitoring of the condition of the fuel line assembly and helps to determine when its condition has degraded to the point that an action of repair or replacement needs to be taken.

Figure 4:
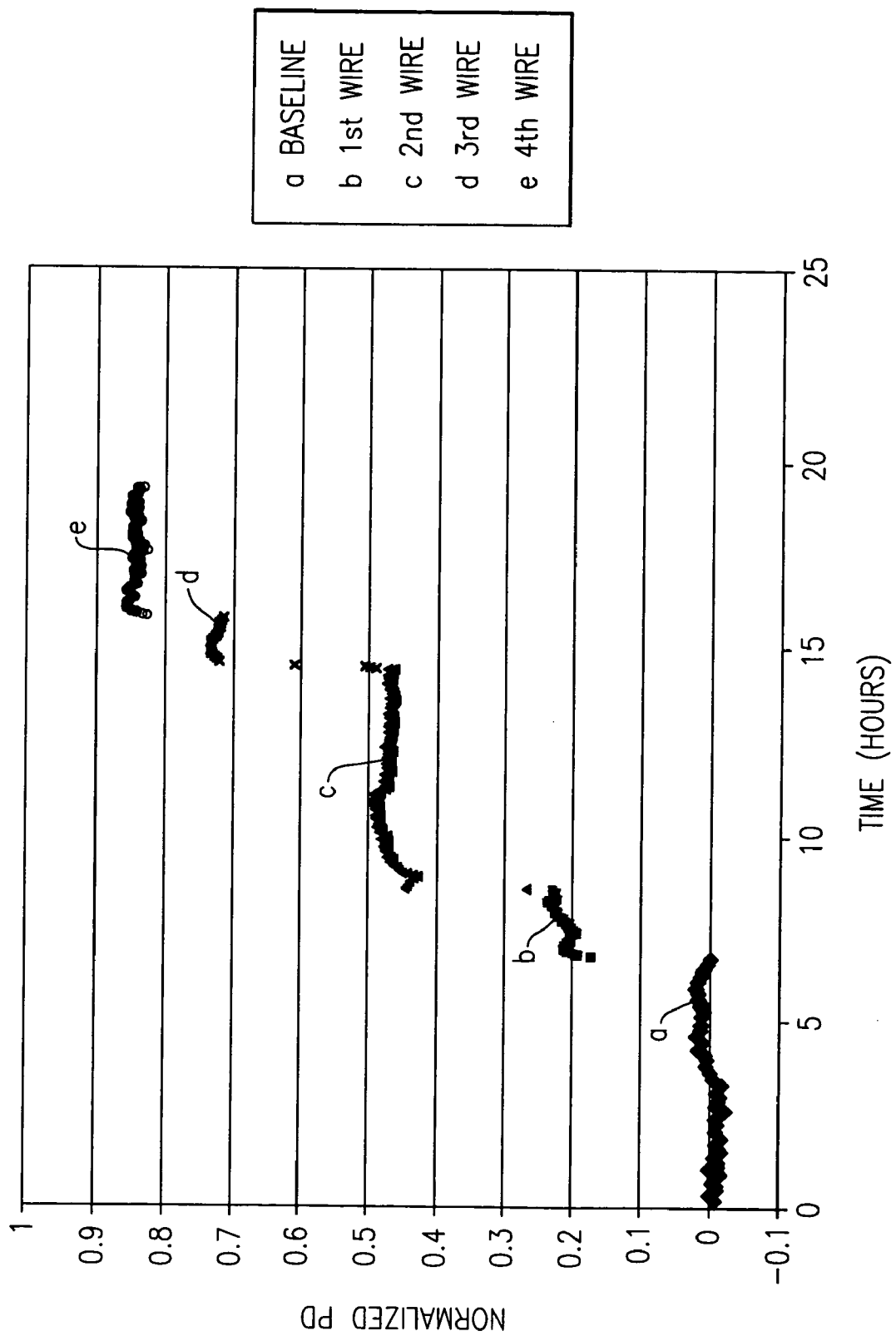
FIG. 4 is a graphical illustration of resultant measurements which are made in accordance with a preferred embodiment of the invention.

For purposes of demonstrating the concept, a deterioration of the stainless steel wire braid 23 was simulated by progressively cutting 4 braid wires and recording the voltage drop change that occurred as a result thereof. The results are shown in FIG. 4 wherein the normalized potential difference (PD) is recorded as a function of time.

First, a reference voltage was measured to calibrate the apparatus to show that, in the undegraded condition, the voltage drop, is indicated as zero units as shown at curve a. Subsequently, a first wire was cut and the voltage drop was measured to be 0.2 units as shown at curve b. Similarly, a second, a third and a fourth wire was successively cut and the respective voltage drops measured were as shown at curves c, d and e, respectively. It will be thus seen that an approximate 0.2% change in the voltage was detected for each wire cut. This voltage increase is well above the ambient noise of the system and a clear indication of damage progression. The present invention uses a threshold valve to determine when the fuel line assembly 21 should be replaced, namely the number of mesh wires that would need to break before the PTFE core integrity was compromised. Thus, the instrumentation can be used to automatically measure and detect when the number of broken wires approaches the limit. Alternatively, the rate of breakage of wires can be monitored to determine whether this compares favorably with a normal rate, and if the rate exceeds the normal rate, then one may find it desirable to replace the fuel line assembly at an earlier time than would normally be indicated by the approach of allowing the number to approach the limit, or, alternatively, to use this information to determine the reason for the accelerated rate of failures in the individual wire strands.

Although the instrumentation as described hereinabove uses a DC potential system, it should be understood that a similar AC potential system could also be utilized.

It should also be recognized that, although the present method has been described in terms of use with a fuel line assembly, it is equally applicable to various other components which may be subject to degradation by any means such as cracking, pitting, corrosion, erosion, wear and so forth.

Representative applications of the present method include but are not limited to the following. In bearings, failure due to wear and loss of raceway material can be detected as a measurable change in resistance. A change in resistance across a turbine blade or vane can be used as an indicator of cracking, erosion, creep or foreign object damage. Pressure vessels such as engine cases, undergoing pressure cycles, can be monitored for low cycle fatigue (LCF) cracks in high stress locations. On a larger scale, large aluminum sections of airplane fuselage could be monitored to detect and warn of fatigue cracks at rivet holes. By continuously monitoring these life limiting locations using the potential drop method as described hereinabove, service life can be safely extended and field issues can be monitored as part of a comprehensive maintenance program.

While the present invention has been particularly shown and described with reference to a preferred embodiment as illustrated in the drawings, it will be understood by one skilled in the art that various changes in detail may be effected therein without departing from the true spirit and scope of the invention as defined by the claims.

We claim:

1. A method of detecting cracks and monitoring crack propagation that may occur along the length of a component that is subject to cracking, comprising the steps of:
   applying an electrical potential across the entire length of said component;
   measuring the electrical potential drop across said length to obtain a base line indicator;
   subsequently monitoring the electrical potential drop across said length to obtain a subsequent reading; and
   determining the degree of cracking that has occurred in the component by comparing said base line indicator to said subsequent reading; and establishing a predetermined level of cracking and comparing said determined degree of cracking with said predetermined level to determine the useful life of the component.

2. A method as set forth in claim 1 wherein the steps of applying a potential across said length of said component and obtaining a base line indicator is accomplished when said component is in a non-cracked condition.

3. A method as set forth in claim 1 wherein the steps of subsequently monitoring the electrical potential across said length is accomplished while maintaining said electrical potential across said length to obtain potential drop readings relative to said length.

4. A method as set forth in claim 3 wherein said determining step is accomplished by obtaining a difference reading between said potential drop readings and said baseline indicator.

5. A method as set forth in claim 1 wherein the electrical potential is applied between a pair of tube connectors at the respective ends of said component length.

6. A method of detecting cracks and monitoring crack propagation that may occur along the length of a component that is subject to cracking, comprising the steps of:
    applying an electrical potential across the entire length of said component;
    measuring the electrical potential drop across said length to obtain a base line indicator;
    subsequently monitoring the electrical potential drop across said length to obtain a subsequent reading;
    determining the degree of cracking that has occurred in the component by comparing said base line indicator to said subsequent reading; and
    establishing a predetermined level of cracking and comparing said potential drop readings with said predetermined level to determine the useful life of the component.

7. A method as set forth in claim 6 and including the additional step of replacing the component when the useful life has expired.

8. A method as set forth in claim 6 wherein said component is an aircraft gas turbine engine component.

9. A method as set forth in claim 8 wherein said component is a flexible hose.

10. A method of diagnosing the useful life of a component that is susceptible to cracking and eventual failure, comprising the steps of:
    while applying an electrical potential across the entire length of the component, measuring the electrical resistance across said length to obtain a base line potential drop reading;
    while continuing to maintain the same electrical potential across said length during normal use, continuing to measure the potential drop thereacross as it changes as a result of cracking; and
    comparing said changes with a predetermined value to predict the time in which the component is likely to fail.

11. A method as set forth in claim 10 wherein the steps of applying an electrical potential across the entire length of the component and measuring the electrical resistance across said length to obtain a base line potential drop reading is accomplished when said component is in a non-cracked condition.

12. A method as set forth in claim 10 and including the step of replacing the component prior to the time in which the component has been determined to be likely to fail.

13. A method as set forth in claim 10 wherein said component is an aircraft gas turbine engine component.

14. A method as set forth in claim 13 wherein said component is a flexible hose.

15. A method as set forth in claim 10 wherein the electrical potential is applied between a pair of tube connectors at the respective ends of said component length.

16. Apparatus for detecting and monitoring crack propagation that may occur along a length of a component which is subject to cracking comprising:
    a voltage source applied at two spaced points at the ends of the entire length of said component so as to present a voltage drop across said length;
    a volt meter for measuring the voltage drop across the length, first to obtain a base measurement when the component is in a non-cracked condition, and subsequently to obtain a damage assessment measurement when it is in a cracked condition; and
    a recording device for recording both said base measurement and said damage assessment measurement to determine the extent of cracking for purposes of repair/replacement of the component; and
    establishing a predetermined level of cracking and comparing said damage assessment measurement with said predetermined level to determine the useful life of the component.

17. An apparatus as set forth in claim 16 wherein said voltage source is a DC source.

18. An apparatus as set forth in claim 16 wherein said component is a flexible fuel line assembly having an outer sheath structure composed of wire braids, with individual strands that are subject to failure.

19. An apparatus as set forth in claim 18 wherein said flexible fuel line assembly further includes an internal tube disposed within said steel wire braid.

20. An apparatus as set forth in claim 19 wherein said internal tube is composed of PTFE.

21. A method of detecting and monitoring crack propagation that may occur along the length of a component that is subject to cracking from operational use, comprising the steps of:
    identifying the length in which the failure is likely to occur in the component;
    applying a voltage across said entire length;
    measuring the voltage drop across said length both prior to and after the component has undergone cracking; and
    on the basis of those measurements, determining when the component should be replaced.

22. A method as set forth in claim 21 wherein said measurement taken prior to the component having undergone cracking is used as a base value that is used for the measuring step.

23. A method as set forth in claim 21 wherein said measuring steps include the steps of taking of a plurality of measurements to indicate the progression of a cracking.

24. A method as set forth in claim 23 wherein said plurality of measurements are compared to obtain an indication of the rate of cracking.

25. A method as set forth in claim 21 and including the further step of recording the measurements taken.

26. A method as set forth in claim 21 wherein said component is an aircraft gas turbine engine.

27. A method as set forth in claim 26 wherein said component is a flexible hose.

28. A method as set forth in claim 21 wherein the electrical potential is applied between a pair of tube connectors at the respective ends of said component length.

* * * * *